(12) United States Patent
Rezach

(10) Patent No.: US 11,298,163 B2
(45) Date of Patent: Apr. 12, 2022

(54) INTERNAL BREAKOFF SET SCREW AND DRIVER

(71) Applicant: Warsaw Orthopedic, Inc., Warsaw, IN (US)

(72) Inventor: William A. Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 297 days.

(21) Appl. No.: 16/391,264

(22) Filed: Apr. 22, 2019

(65) Prior Publication Data
US 2020/0330137 A1    Oct. 22, 2020

(51) Int. Cl.
| | | |
|---|---|---|
| A61B 17/70 | (2006.01) | |
| F16B 23/00 | (2006.01) | |
| A61B 17/88 | (2006.01) | |
| A61F 2/46 | (2006.01) | |
| A61B 17/86 | (2006.01) | |

(52) U.S. Cl.
CPC ...... *A61B 17/7082* (2013.01); *A61B 17/8888* (2013.01); *A61F 2/4603* (2013.01); *F16B 23/0069* (2013.01); *A61B 17/8615* (2013.01)

(58) Field of Classification Search
CPC .................. A61B 17/7082; F16B 23/0069
USPC ............ 411/347–348, 407, 408; 81/448, 452
See application file for complete search history.

(56) References Cited

U.S. PATENT DOCUMENTS

| | | | | |
|---|---|---|---|---|
| 4,911,593 A | * | 3/1990 | Kephart | F16B 23/0038 411/403 |
| 5,017,069 A | * | 5/1991 | Stencel | F16B 21/086 411/403 |
| 5,291,811 A | * | 3/1994 | Goss | B25B 13/065 411/404 |
| 5,456,145 A | * | 10/1995 | Cosenza | B25B 27/143 81/448 |
| 5,797,911 A | | 8/1998 | Sherman et al. | |
| 5,941,885 A | * | 8/1999 | Jackson | A61B 17/7082 606/104 |
| 7,625,394 B2 | | 12/2009 | Molz, IV et al. | |
| 7,722,623 B2 | * | 5/2010 | Franks | A61B 17/7091 606/104 |
| 7,846,167 B2 | * | 12/2010 | Garcia | A61B 17/862 606/104 |
| 7,914,559 B2 | | 3/2011 | Carls et al. | |
| 7,967,821 B2 | | 6/2011 | Sicvol et al. | |
| 7,967,828 B2 | * | 6/2011 | Moore | A61B 17/7091 606/99 |
| 8,016,836 B2 | | 9/2011 | Corrao et al. | |
| 8,100,909 B2 | * | 1/2012 | Butler | A61B 17/7035 606/60 |

(Continued)

*Primary Examiner* — Nicholas W Woodall
(74) *Attorney, Agent, or Firm* — Fox Rothschild LLP

(57) ABSTRACT

An approach is provided for engaging a set screw to an implant. The approach includes a surgical instrument. The surgical instrument may include a shaft having an elongated rigid structure, and a driver head positioned on a distal end of the surgical instrument. The driver head may include at least one groove or at least one protrusion extending in a longitudinal direction of the surgical instrument and a pin positioned at least partially within the driver head. The pin may be configured to deploy and retract in a lateral direction from with the driver head portion.

18 Claims, 9 Drawing Sheets

(56) References Cited

U.S. PATENT DOCUMENTS

| | | | |
|---|---|---|---|
| 8,105,328 B2* | 1/2012 | Protopsaltis | A61B 17/7091 606/86 A |
| 8,262,662 B2 | 9/2012 | Beardsley et al. | |
| 8,377,100 B2* | 2/2013 | Jackson | A61B 17/685 606/264 |
| 8,992,544 B2* | 3/2015 | Sasing | A61B 17/7077 606/104 |
| 9,072,563 B2 | 7/2015 | Garcia et al. | |
| 9,402,673 B2 | 8/2016 | Cormier et al. | |
| 9,579,139 B2 | 2/2017 | Cormier et al. | |
| 9,668,784 B2 | 6/2017 | Brumfield et al. | |
| 9,827,024 B2 | 11/2017 | Cormier et al. | |
| 9,943,342 B2 | 4/2018 | Tanaka et al. | |
| 10,149,710 B2 | 12/2018 | Tanaka et al. | |
| 2014/0066945 A1* | 3/2014 | Humphreys | A61B 17/8888 606/104 |

* cited by examiner

INTERNAL BREAKOFF SET SCREW AND DRIVER

BACKGROUND

Certain surgeons may prefer to use breakoff set screws when fastening a rod to a collar of a spinal implant. Breakoff set screws may be preferred, for example, to avoid under and over torqueing the set screw, stripping the set screw, breaking the set screw, or breaking the screw or the vertebra. Breakoff set screws may be, for example, external hex breakoff set screws. An example of a multiaxial screw including a breakoff screw is set forth in U.S. Pat. No. 5,797,911, which is incorporated herein by reference in its entirety. However, in some cases, external hex breakoff set screws cannot be used due to geometry interference issues. To accommodate for interference issues, the set screws may be used that have internal drive features, such as a hex shaped recess or a hexalobe shaped recess within the distal end of the set screw. However, when breakoff heads with internal drive features are separated from their set screws, the internal drive features prevent the separated breakoff heads from being stacked on a magazine of a breakoff driver. Moreover, for the cases in which multiple styles of screws are used within a single construct, it may be cumbersome to repeatedly switch out the breakoff driver or the bit of the break off driver to accommodate the various sized set screws and internal drive features.

SUMMARY

The present disclosure relates generally to spinal stabilization systems, and more particularly, to surgical instruments for spinal stabilization systems.

In one or more embodiments, the disclosed technology relates to a surgical instrument including a shaft having an elongated rigid structure, and a driver head positioned on a distal end of the surgical instrument. In one or more cases, the driver head may include at least one groove or at least one protrusion extending in a longitudinal direction of the surgical instrument and a pin positioned at least partially within the driver head. In one or more cases, the pin may be configured to deploy and retract in a lateral direction from with the driver head portion.

In one or more embodiments, the disclosed technology relates to a system for engaging a set screw to an implant. In one or more cases, the system may include a set screw including a breakoff head and a threaded portion coupled together via a breakoff region. In one or more cases, the breakoff head may include at least one interlocking portion. In one or more cases, the system may include a surgical instrument. In one or more cases, the surgical instrument may include a shaft having an elongated rigid structure, and a driver head positioned on a distal end of the surgical instrument. In one or more cases, the driver head may include at least one interlocking portion extending in a longitudinal direction of the surgical instrument and a pin positioned at least partially within the driver head. In one or more cases, the at least one interlocking portion of the driver head may be configured to interlock with the at least one interlocking portion of the breakoff head. In one or more cases, the pin may be configured to deploy and retract in a lateral direction from with the driver head.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

Figure 1A:
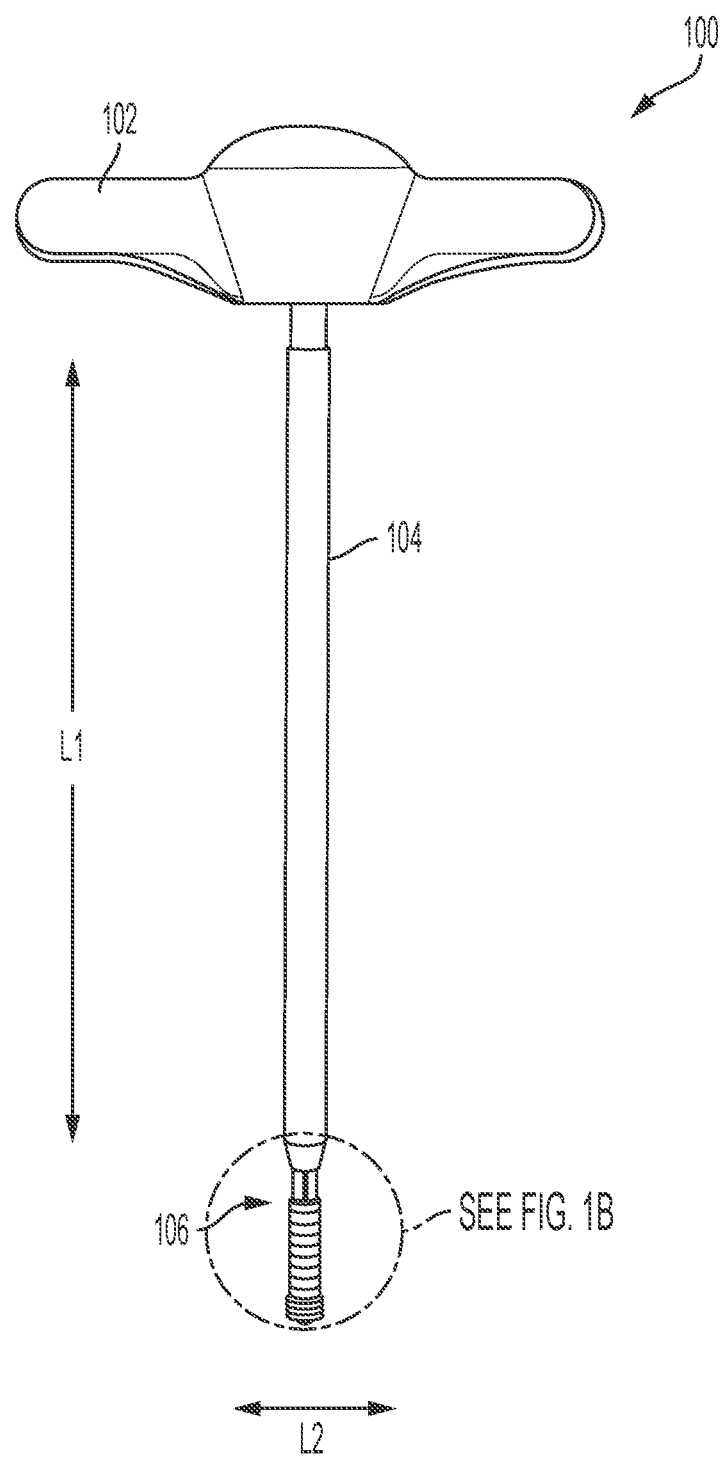
FIG. 1A is a side view illustrating an embodiment of a breakoff driver.

The following discussion omits or only briefly describes certain conventional features related to spinal stabilization systems, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to spinal stabilization systems, and more particularly, to surgical instruments for spinal stabilization systems. Embodiments of the devices and methods are described below with reference to the Figures.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g, all described acts or events may not be necessary to carry out the techniques).

Figure 1B:
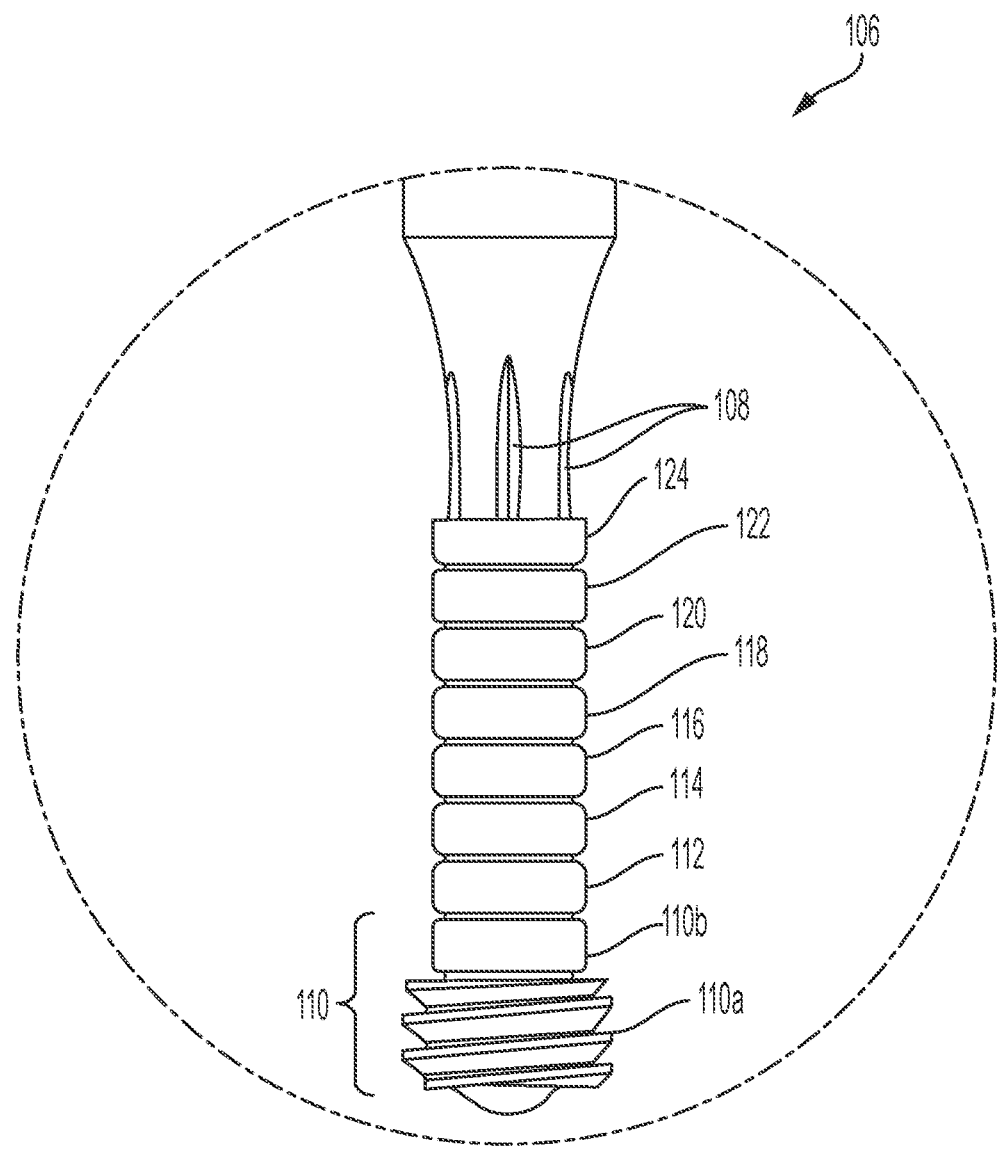
FIG. 1B illustrates an enlarged view of an embodiment of a magazine retention portion.
Figure 2A:
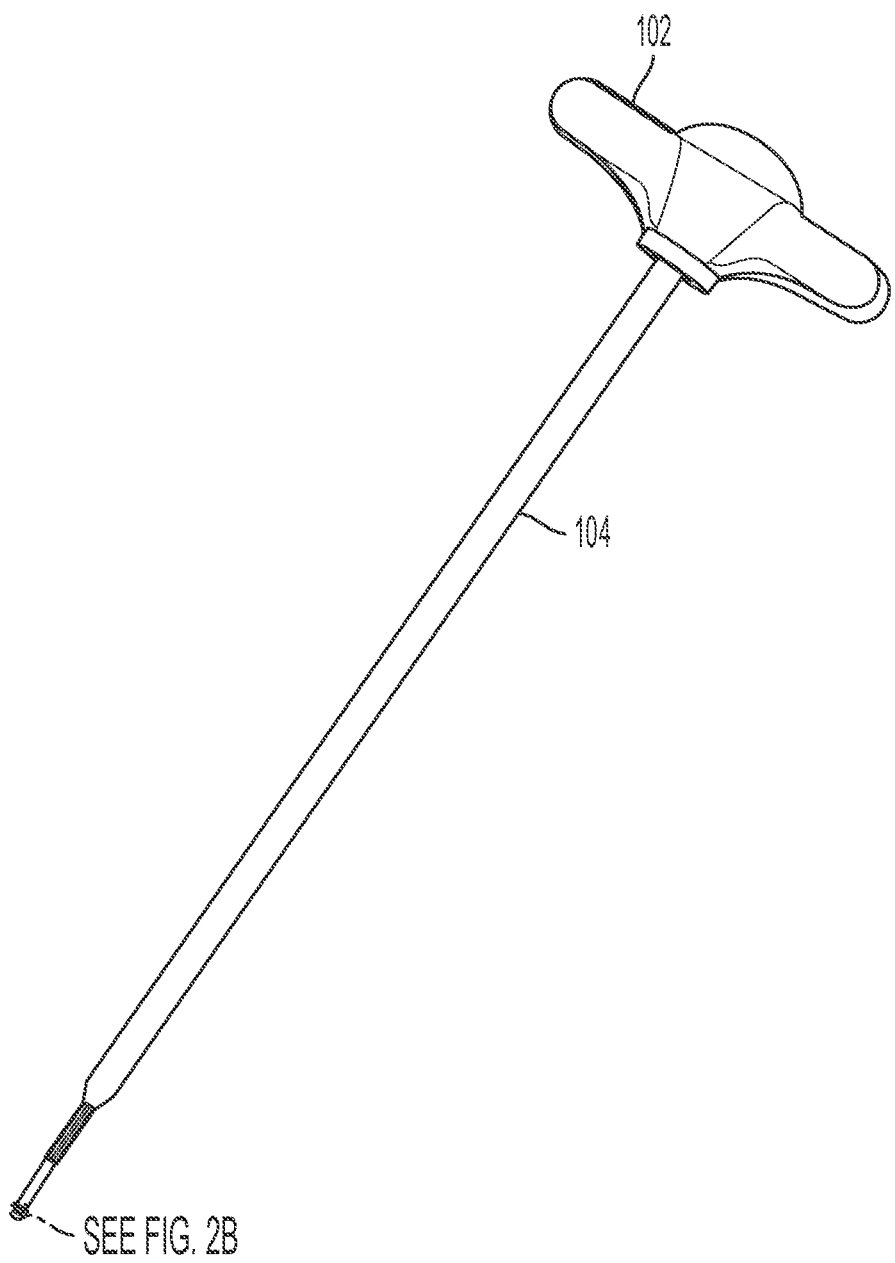
FIG. 2A is a side view illustrating an embodiment of the breakoff driver.
Figure 2B:
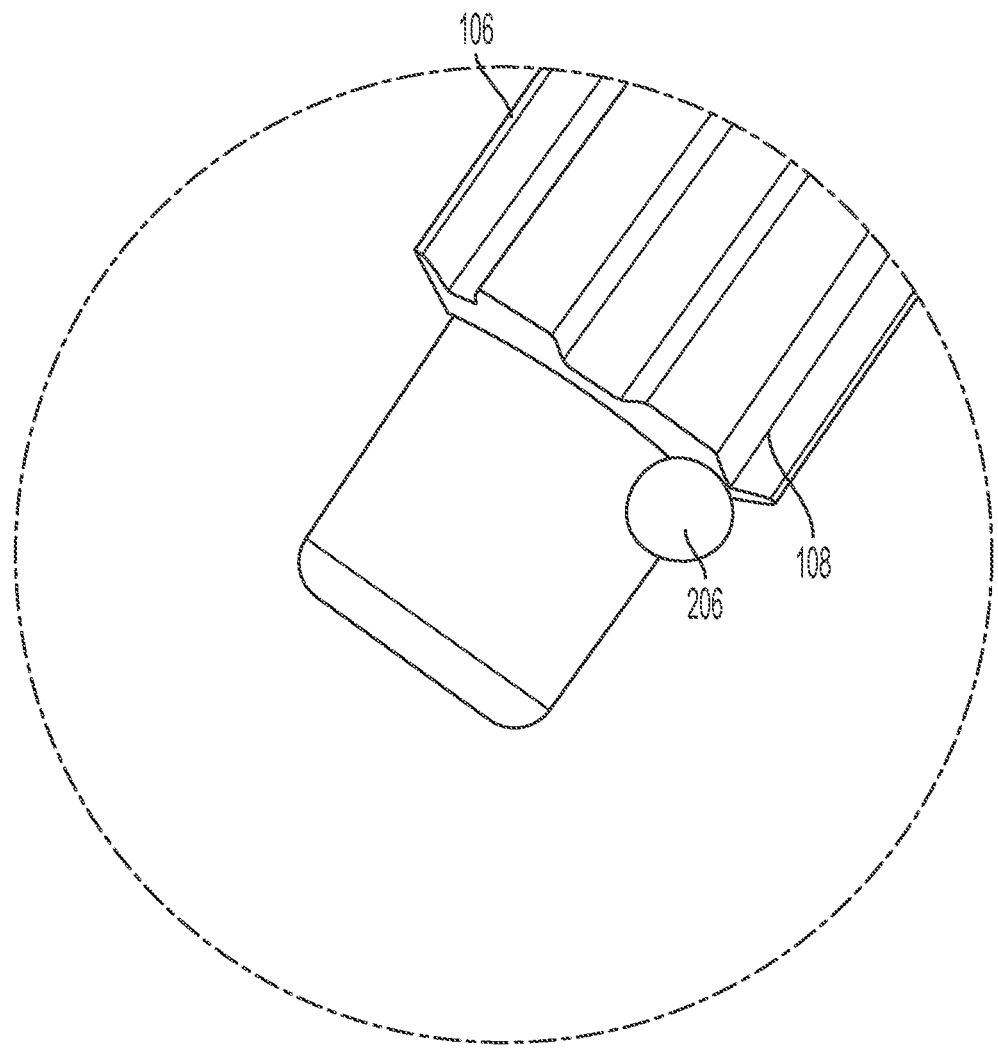
FIG. 2B illustrates an enlarged view of an embodiment of a distal end of the breakoff driver.
Figure 3A:
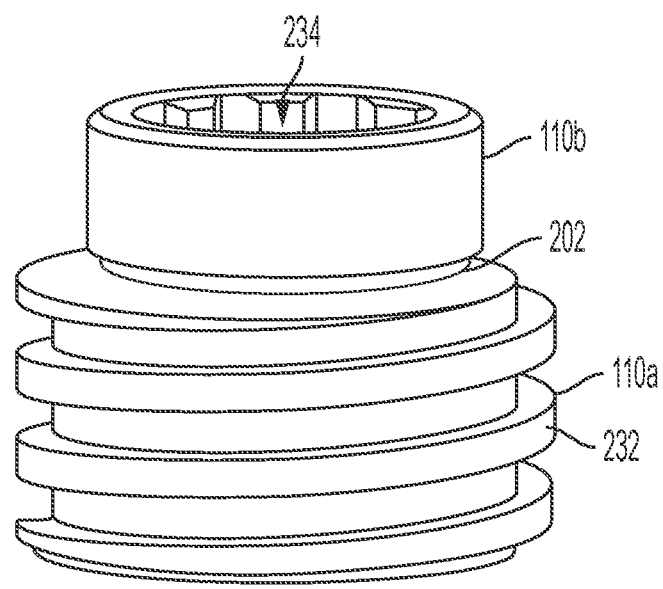
FIG. 3A is an isometric view of an embodiment of a universal set screw.
Figure 3B:
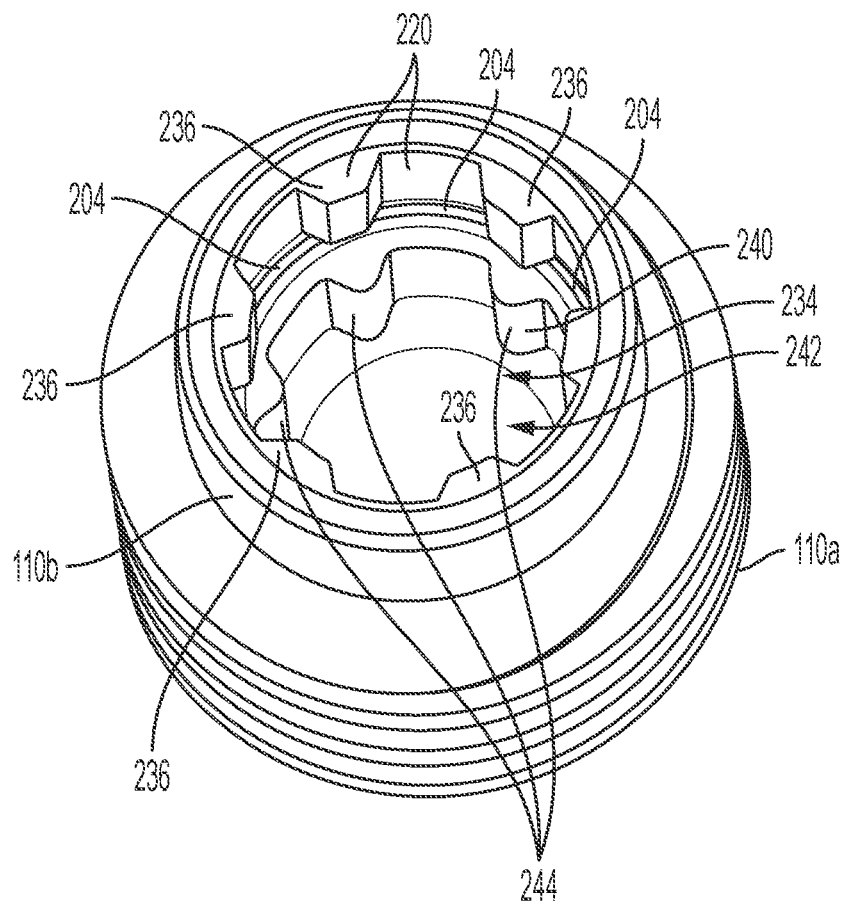
FIG. 3B is another isometric view of an embodiment of the universal set screw.
Figure 4A:
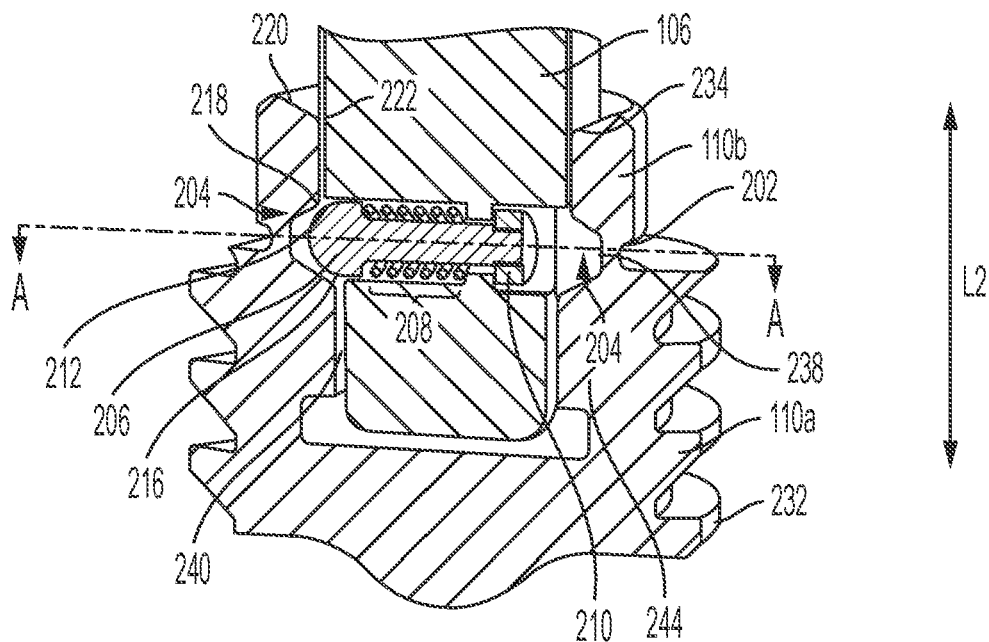
FIG. 4A is a cross-sectional side view of an embodiment of the breakoff driver inserted in the universal set screw.
Figure 4B:
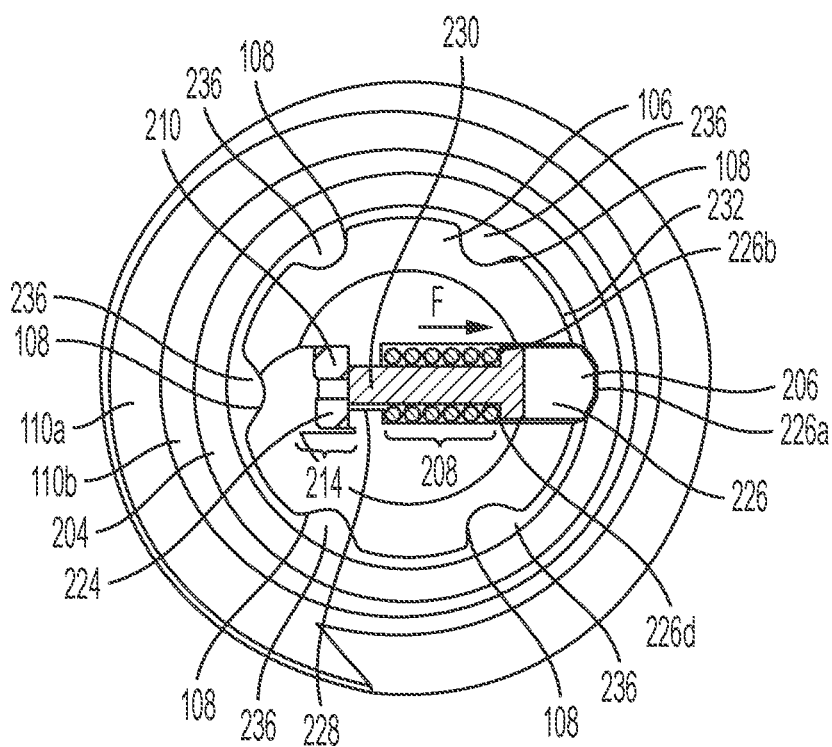
FIG. 4B is a cross-sectional top view, taken along A-A in FIG. 4A, of an embodiment of the breakoff driver inserted in the universal set screw.
Figure 5D:
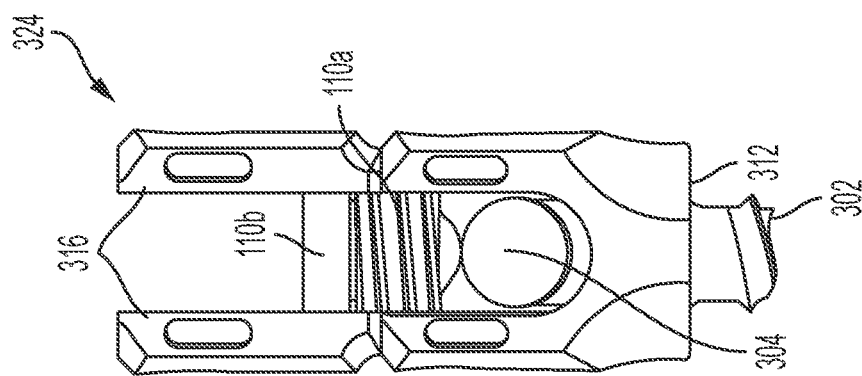
FIGS. 5A, 5B, 5C, and 5D illustrate an example of the universal set screw being engaged with a variety of implants.
Figure 5C:
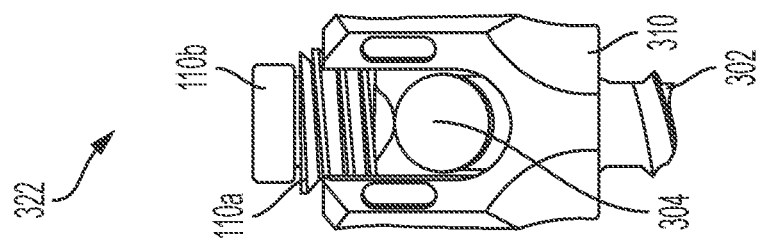
Figure 5B:
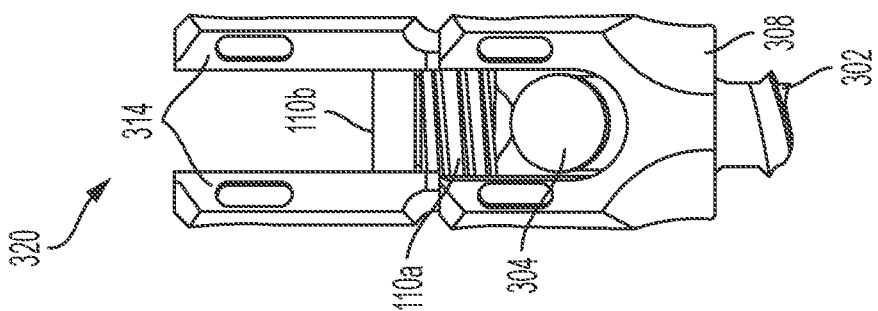
Figure 5A:
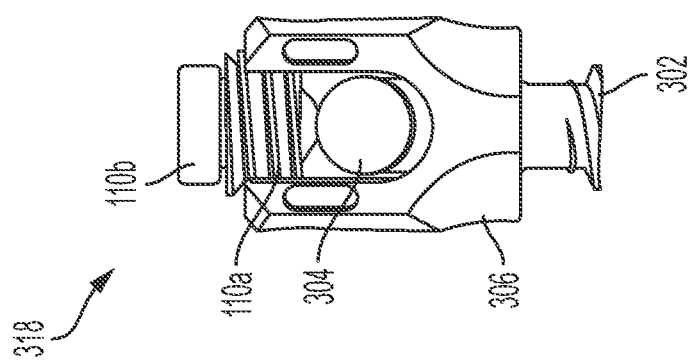

FIG. 1A is a side view illustrating an embodiment of a breakoff driver 100. FIG. 1B illustrates an enlarged view of an embodiment of a magazine retention portion 106. FIG. 2A is a side view illustrating an embodiment of the breakoff driver 100. FIG. 2B illustrates an enlarged view of an embodiment of a distal end of the breakoff driver 100. FIG. 3A is an isometric view of an embodiment of breakoff set screw such as, for example, a universal breakoff set screw 110 ("set screw 110"). FIG. 3B is another isometric view of an embodiment of the set screw 110. FIG. 4A is a cross-sectional side view of an embodiment of the breakoff driver 100 inserted in the set screw 110 ("set screw 110"). FIG. 4B is a cross-sectional top view, taken along A-A in FIG. 4A, of an embodiment of the breakoff driver 100 inserted in the set screw 110. FIGS. 3A, 3B, 3C, and 3D illustrate an example of the set screw 110 being engaged with a variety of implants.

In one or more embodiments, the breakoff driver 100 includes an optional handle 102; a driver head, such as a magazine retention portion 106; and a shaft 104. The shaft 104 may be an elongated rigid member configured to connect the handle 102 and the magazine retention portion 106. The handle 102 and the magazine retention portion 106 may be disposed at opposite ends of the shaft 104. In one or more cases, the shaft 104 may have a linear shape. In one or more other cases, the shaft 104 may have a curved shape. In one or more cases, the handle 102 may be fixed to the shaft 104. In one or more other cases, the handle 102 may be removably attached to the shaft 104. The handle 102 may provide a grip for a user to manipulate the magazine retention portion 106.

The shaft 104 and the magazine retention portion 106 may be, individually or collectively, fabricated from materials such as stainless steel alloys, commercially pure titanium, titanium alloys, Grade 5 titanium, super-elastic titanium alloys, cobalt-chrome alloys, stainless steel alloys, and their combinations.

In one or more embodiments, the magazine retention portion 106 may be an elongated rigid member disposed on the distal end of the breakoff driver 100. The magazine retention portion 106 may include a pin 206 configured to deploy and/or retract from within the magazine retention portion 106, as shown in FIGS. 2A and 2B. In one or more cases, the pin 206 may be configured to deploy and/or retract perpendicular to the longitudinal direction $L_1$ of the magazine retention portion 106. In one or more other cases, the pin 206 may be configured to deploy and/or retract in a lateral direction $L_2$ of the magazine retention portion 106.

In one or more cases, the pin 206 may be spring loaded. For example, an elongated member 230 of the pin 206 may extend through a dividing wall 228, in which a first end 224 of the pin 206 is located on one side of the dividing wall 228 and a second end 226 of the pin 206 is located on the opposite side of the dividing wall 228. In one or more cases, the elongated member 230 may be a cylindrical rigid member and may have a diameter smaller than the diameter of the second end 226. The portion of the first end 224 of the pin 206 may include a stopping member 210 that prevents the pin 206 from fully exiting the magazine retention portion 106 in the direction of the force $F_1$ generated by a spring 208. The second end 226 of the pin 206 may include a semispherical shape 226a on the distal portion of the second end 226, and flat surfaces 226b on a proximal portion of the second end 226. The flat surfaces 226b may be located on both sides of the elongated member 230. The pin 206 may be inserted through the spring 208, in which one end of the spring 208 is configured to contact the dividing wall 228 and the opposite end of the spring 208 is configured to contact the flat surfaces 226b of the second end 226. The spring 208 may be configured to apply a force $F_1$ against the flat surfaces 226b to move a portion of the second end 226 beyond the outer surface 232 of the magazine retention portion 106.

In one or more embodiments, the set screw 110 includes a threaded portion 110a and a breakoff head 110b coupled to one another via a breakoff region 202. The threaded portion 110a may have external threads around the outer surface 232 of the set screw 110. The threaded portion 110a may be configured to attach to a collar, such as collar 306, 308, 310, and/or 312, and capture a longitudinal member 304. The set screw 110 may be sized to fit within the collar.

The breakoff region 202 may extend circumferentially around the outer surface 232 of the set screw 110. In one or more cases, a recessed area 204 may be formed on a side of the breakoff head 110b opposite to the breakoff region 202. In one or more cases, the recessed area 204 may extend circumferentially around the inner surface 222 of the set screw 110. In one or more other cases, the recessed area 204 may extend circumferentially and intermittently around the inner surface 222 of the set screw 110. The recessed area 204 may be large enough to receive a portion of the second end 226 of the set screw 110. For example, the recessed area 204 may be configured to receive the semispherical shaped portion 226a of the second end 226. In one or more cases, the surface 238 of the recessed area 204 may be formed in a curved shape. The curved shape may be configured to correspond to the semispherical shaped portion 226a of the second end 226. In one or more other cases, the surface 238 of the recessed area 204 may be formed in a semi-trapezoidal shape.

In one or more cases, at least a portion of the second end 226 of the pin 206 may be configured, in a deployed state, to extend beyond the outer surface 232 of the magazine retention portion 106. In a retracted state, the pin 206 may be housed within the magazine retention portion 106. In one or more cases, the pin 206 may be aligned to protrude through a portion of the groove 108 of the magazine retention portion 106. In one or more other cases, the pin 206 may be aligned to protrude through a portion of the outer surface 232 of the magazine retention portion 106 that does not include a groove 108.

In one or more cases, the diameter of the magazine retention portion 106 may be large enough to fit snugly within an opening 234 of breakoff head 110b of the set screw 110. For example, the diameter of the magazine retention portion 106 may be large enough such that a portion of the distal end of the magazine retention portion 106 may fit within at least a portion of the breakoff head 110b. The outer circumferential surface 232 of the magazine retention portion 106 may be corrugated or formed in a hexalobe shape, such that the plurality of grooves, such as groove 108, may be circumferentially disposed around the outer surface 232 of the magazine retention portion 106. The grooves 108 may extend in the longitudinal direction $L_1$ of the magazine retention portion 106. The grooves 108 may be configured to align the breakoff driver 100 within the grooves 236 of the set screw 110. The grooves 108 may act as a guide for a broken-off breakoff head to slide along the magazine retention portion 106. The groove 108 may be formed into the magazine retention portion 106 in a variety of shapes, such as an arced or curved shape, a square shape, a triangular shape, or the like, when viewed from a top view of the magazine retention portion 106. In one or more cases, adjacent grooves 108 may be separated by a protrusion. In one or more other cases, the magazine retention portion 106 includes only one groove.

The inner surface 222 of the breakoff head 110b may be corrugated or in a hexalobe shape, such that a plurality of protrusions 236 are positioned in a longitudinal direction $L_2$ of the breakoff head 110b and are arranged circumferentially around the inner surface 222 of the breakoff head 110b. In one or more cases, adjacent protrusions 236 may be separated by a groove. In one or more cases, the plurality of protrusions 236 on the inner surface 222 of the breakoff head 110b may be configured to interlock with the plurality of grooves 108 arranged around the magazine retention portion 106. Additionally, the plurality of grooves, formed by the protrusions 236, of the breakoff head 110b may be configured to interlock with the plurality of protrusions, formed by the grooves 108, of the magazine retention portion 106. By interlocking the plurality of protrusions 236 of the breakoff head 110b and the magazine retention portion 106, the set screw 110 may be prevented from rotating in a clockwise or counterclockwise manner about the magazine retention portion 106. In one or more cases, an interlocking portion of the breakoff head may be a protrusion 236, and an interlocking portion of the magazine retention portion 106 may be a groove 108. In one or more cases, an interlocking portion of the breakoff head may be a groove, and an interlocking portion of the magazine retention portion 106 may be a protrusion.

In one or more embodiments, the opening 234 of the breakoff head 110 may be larger than an opening 242 of the threaded portion 110a. In one or more cases, the inner surface 240 of the threaded portion 110a may be corrugated or in a hexalobe shape, such that a plurality of protrusions 244 are positioned in a longitudinal direction $L_2$ of the threaded portion 110a and are arranged circumferentially around the inner surface 240 of the breakoff head 110a. In one or more cases, after the breakoff head 110b is broken off the threaded portion 110a, another screw driver may be inserted into the opening 242 of the threaded portion 110a to tighten or loosen the set screw 110.

In one or more embodiments, the magazine retention portion 106 may be configured to break off the breakoff head 110b from the threaded portion 110a of the set screw 110. In one or more examples, the set screws 110 may be fastened into an implant, such as a uniaxial screw (UNI) 318, a multiaxial screw (MAS) 320, a reduction head multiaxial screw (RMAS) 322, or an extended tab MAS 324 as shown in FIGS. 3A-3D. The implant may be fixed to a bony anatomy, such as a vertebra. To break off the breakoff head 110b from the threaded portion 110a of the set screw 110, a user inserts the magazine retention portion 106 into the opening 234 of the breakoff head 110b, such that the inner surface 222 of the breakoff head 110b interlocks with the outer surface 232 of the magazine retention portion 106, as described above. Having interlocked the breakoff head 110b and the magazine retention portion 106 in a circumferential direction, the user may turn the handle 102 in a clockwise or counterclockwise manner, thereby rotating the shaft 104 and the magazine retention portion 106. At a certain amount of torque, generated by rotating the breakoff driver 100 in the set screw 110, the breakoff head 110b may break off from the threaded portion 110a of the set screw 110. In one or more cases, the breakoff head 110b may break off from the threaded portion 110a at a torque ranging from at or about 8 Newton meter (Nm) to at or about 12 Nm.

In one or more embodiments, the magazine retention portion 106 may be configured to hold one or more broken-off breakoff heads, such as broken heads 112, 114, 116, 118, 120, 122, and 124. In one or more cases, the magazine retention portion 106 may be sized to hold one or more broken-off breakoff heads. For example, the magazine retention portion 106 may be long enough to hold a minimum of six broken-off breakoff heads. In another example, the magazine retention portion 106 may be sized to hold eight broken-off breakoff heads. As each breakoff head is broken off a set screw, the broken-off breakoff heads may stack on one another, such that the earliest broken-off breakoff head is positioned on top of the stack followed by the next earliest broken-off breakoff head.

When the magazine retention portion 106 is inserted into the opening 234 of the set screw 110, the grooves 108 of the magazine retention portion 106 are aligned with the grooves 236 of the breakoff head 110b, and the spring 208 is configured in a deployed state. As the magazine retention portion 106 is inserted into the opening 234 of the set screw 110, a curved bottom 216 of the second end 226 contacts a tapered distal end 220 of the breakoff head 110b. The tapered distal end 220 may taper downwards towards the center of the breakoff head 110b. As the magazine retention portion 106 is inserted farther into the breakoff head 110b, the tapered distal end 220 and/or the inner surface 222 may force the pin 206 to retract within the magazine retention portion 106, thereby compressing the spring 208. When the pin 206 reaches the recessed area 204, the spring 208 forces the pin 206 into a deployed state, in which the pin 206 enters into the recessed area 204.

For the cases in which the breakoff head 110b is broken off the threaded portion 110a, the curved upper surface 218 of the second end 226 protrudes far enough to prevent the separated breakoff head 110b from sliding off the magazine retention portion 106. For the cases in which second breakoff head is separated from a second set screw, the separated second breakoff head forces the first separated breakoff head 110b up the magazine retention portion 106. The separated breakoff heads may stack on top of one another as each separated breakoff head is added to the magazine retention portion 106.

Figure 6:
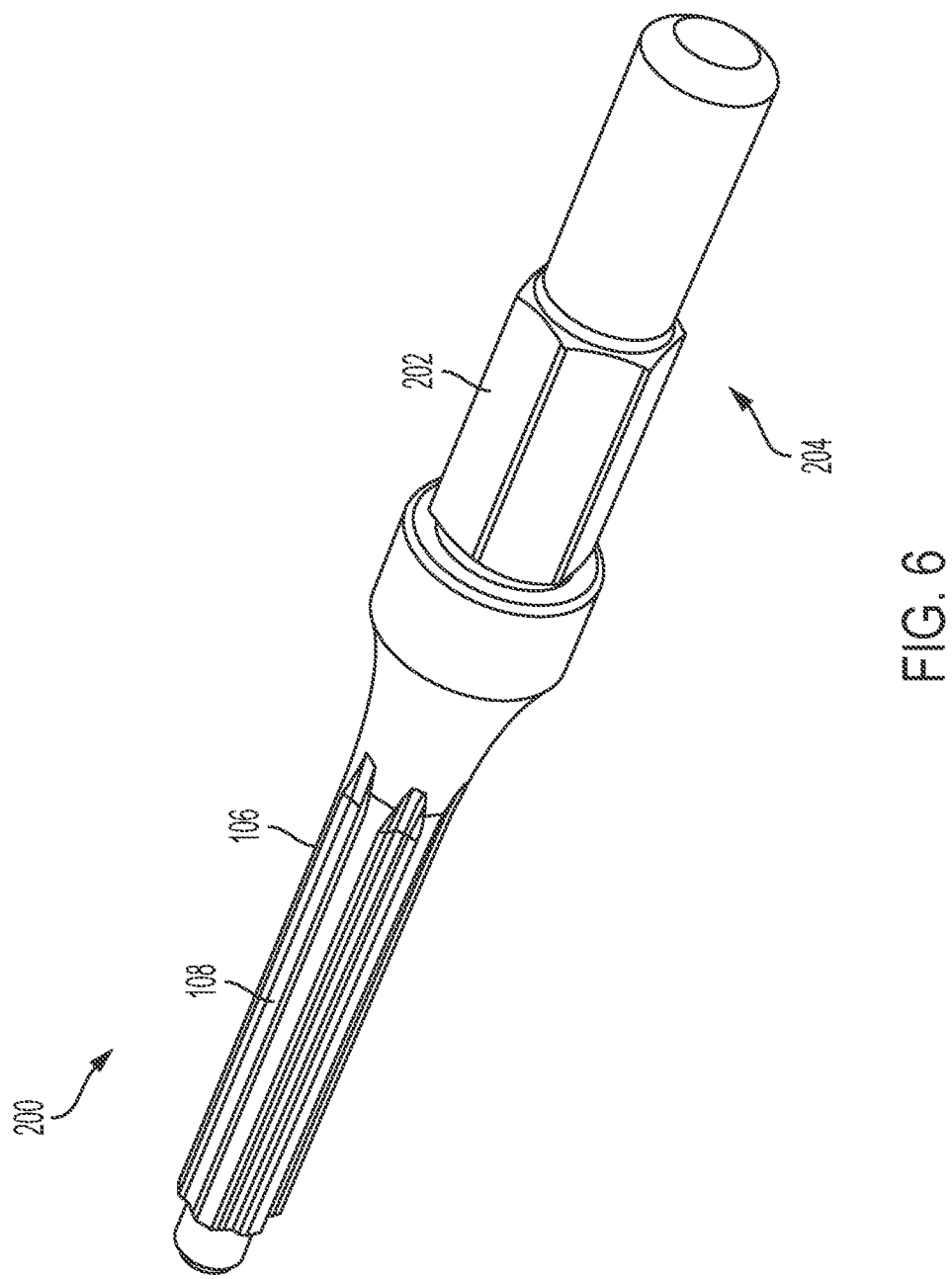
FIG. 6 is a perspective view of an embodiment of a breakoff driver adapter.

FIG. 6 is a perspective view of an embodiment of a breakoff driver adapter 200. In one or more embodiments, the breakoff driver adapter 200 is an elongated member that includes the magazine retention portion 106 disposed on one end of the breakoff driver adapter 200 and a driving receiver 202 disposed on an opposite end of the breakoff driver adapter 200. The magazine retention portion 106 of the breakoff driver adapter 200 includes one or more of the same or similar features as the magazine retention portion 106 of the breakoff driver 100. Accordingly, a description of such features is not repeated. In one or more cases, the driving receiver 202 is configured in an external shape to enable a positive, non-slip engagement with a multi-bit driver. For example, the driving receiver 202 may be formed as a ¼ inch hex bit, in which the insertion end 204 is inserted into a bit receiving portion of the multi-bit driver. The driving receiver 202 may be removably coupled to the multi-bit driver, such that other breakoff driver adapters configured to engage differently shaped set screws may be inserted into the multi-bit driver.

Figure 7:
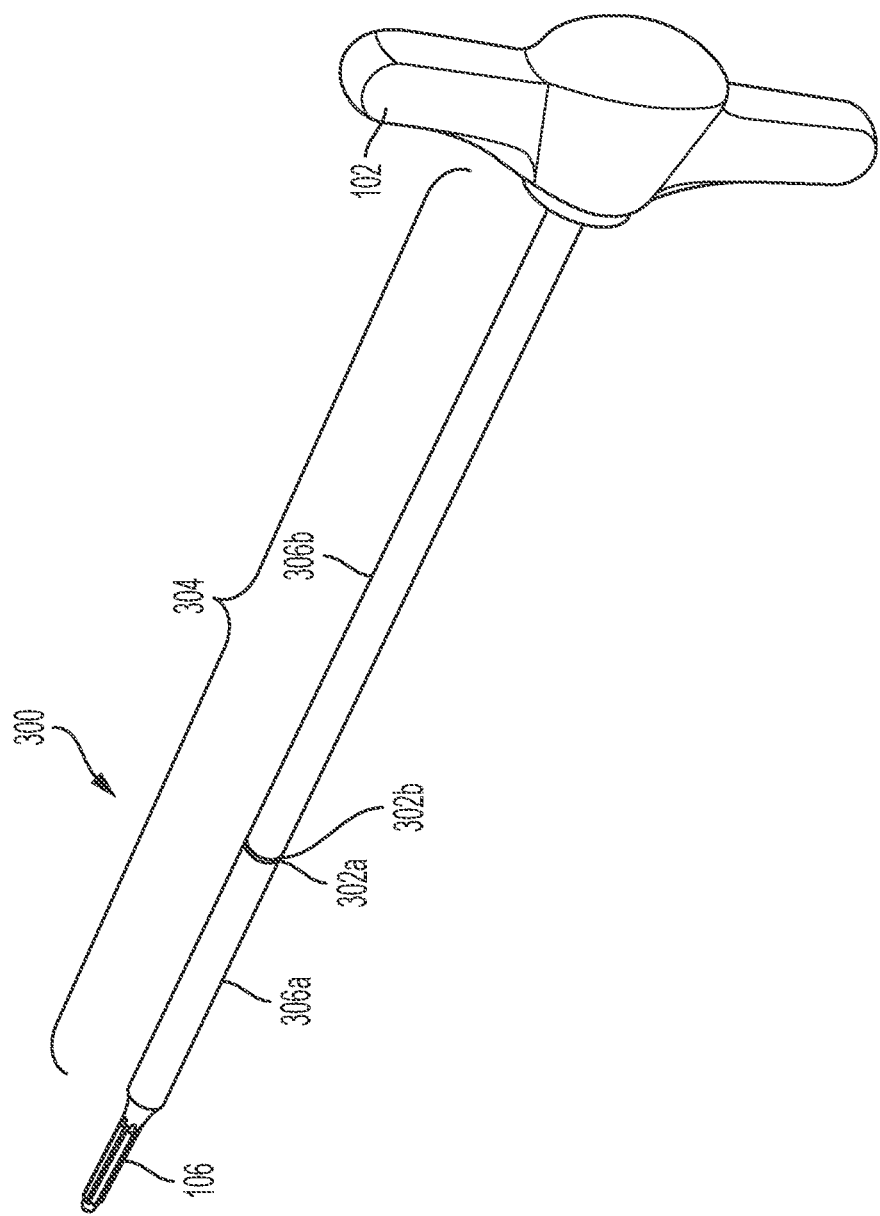
FIG. 7 is a perspective view of an embodiment of another breakoff driver.

FIG. 7 is a perspective view of an embodiment of another breakoff driver 300. In one or more embodiments, the breakoff driver 300 includes the magazine retention portion 106 disposed on one end of the breakoff driver 300 and the optional handle 102 disposed on an opposite end of the breakoff driver 300. The magazine retention portion 106 and the handle 102 of the breakoff driver 300 includes one or more of the same or similar features as the magazine retention portion 106 and the handle 102 of the breakoff driver 100. Accordingly, a description of such features is not repeated.

In one or more cases, the breakoff driver 300 includes a shaft 104. The shaft 304 may be an elongated rigid member configured to connect the handle 102 and the magazine retention portion 106. The handle 102 and the magazine retention portion 106 may be disposed at opposite ends of the shaft 304. In one or more cases, the shaft 304 may have a linear shape. In one or more other cases, the shaft 304 may have a curved shape.

The shaft 304 includes a first shaft portion 306a removably coupled with a second shaft portion 306b. In one or more cases, the magazine retention portion 106 may be coupled with the first shaft portion 306a. The shaft 304 and the magazine retention portion 106 may be, individually or collectively, fabricated from materials such as stainless steel alloys, commercially pure titanium, titanium alloys, Grade 5 titanium, super-elastic titanium alloys, cobalt-chrome alloys, stainless steel alloys, and their combinations. In one or more cases, the handle 102 may be fixed to the second shaft portion 306b. In one or more other cases, the handle 102 may be removably attached to the second shaft portion 306b. In one or more embodiments, the first shaft portion 306a and the magazine retention portion 106 may be manufactured together, and the second shaft portion 306b may be manufactured separate from the first shaft portion 306a and the magazine retention portion 106. Subsequently, the first shaft portion 306a and the second shaft portion 306b may be coupled together, thereby forming the shaft 304. In one or more cases, the first shaft portion 306a includes a protrusion 302a configured to fit within a receiving portion 302b of the second shaft portion 306b. In some cases, the protrusion 302a may have a threaded end configured to mate with a threaded end of the receiving portion 302b. In some other cases, the protrusion 302a may snap fit within the receiving portion 302b. In one or more other cases, the second shaft portion 306b includes a protrusion 302a configured to fit within a receiving portion 302b of the first shaft portion 306a.

As used herein, the term "about" in reference to a numerical value means plus or minus 10% of the numerical value of the number with which it is being used.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A surgical instrument comprising:
a shaft having an elongated rigid structure extending in a longitudinal direction from a first end to a second end, and
a driver head positioned on a distal end of the surgical instrument,
wherein the driver head comprises:
a magazine retention portion extending in the longitudinal direction from the second end towards the distal end of the surgical instrument a distance sufficient for simultaneously storing a plurality of broken-off breakoff head portions of a corresponding plurality of set screws;
at least one groove or at least one protrusion extending in the longitudinal direction along the magazine retention portion,
a coil spring and pin positioned at least partially within the driver head, the coil spring and pin being positioned between the distal end of the surgical instrument and the magazine retention portion, and
wherein the coil spring applies a biasing force urging the pin outward from the driver head in a lateral direction perpendicular to the longitudinal direction such that in a deployed position a head portion of the pin extends laterally farther than a lateral edge of the driver head and in a retracted position the coil spring is compressed within the driver head portion.

2. The surgical instrument of claim 1, further comprising a handle positioned adjacent the first end of the surgical instrument opposite the driver head.

3. The surgical instrument of claim 1, wherein the magazine portion is configured to store a broken-off breakoff head portion of a first set screw while the at least one groove is configured to interlock with at least one groove positioned on an internal surface of an opening of a second set screw.

4. The surgical instrument of claim 1, wherein the magazine portion is configured to store a broken-off breakoff head portion of a first set screw while the at least one protrusion is configured to interlock with at least one groove positioned on an internal surface of an opening of a second set screw.

5. The surgical instrument of claim 1, wherein a distal end portion of the pin comprises a semispherical shape.

6. The surgical instrument of claim 5, wherein the distal end portion of the pin, positioned in the deployed state, is configured to:
retain the plurality of broken-off breakoff head portions of the corresponding plurality of set screws on the magazine retention portion;
prevent the plurality of broken-off breakoff head portions of the corresponding plurality of set screws from sliding off the driver head, and
seat within a cavity of a breakoff area of a first set screw, the first set screw having a breakoff head portion connected to a threaded portion.

7. A system for engaging a set screw to an implant, the system comprising:
a first set screw comprising a first breakoff head and a first threaded portion coupled together via a first breakoff region and a first interlocking portion,
a second set screw comprising a second breakoff head and a second threaded portion coupled together via a second breakoff region and a second interlocking portion; and
a surgical instrument comprising:
a shaft having an elongated rigid structure extending in a longitudinal direction from a first end to a second end, and
a driver head positioned on a distal end of the surgical instrument,
wherein the driver head comprises:
a magazine retention portion extending in the longitudinal direction from the second end towards the distal end of the surgical instrument;

at least one interlocking portion extending in the longitudinal direction along the magazine retention portion, a coil spring and pin positioned within a recessed detent of the driver head between the distal end of the surgical instrument and the magazine retention portion, wherein the at least one interlocking portion of the driver head is configured to interlock with the first interlocking portion of the first breakoff head and/or the second interlocking portion of the second breakoff head, wherein the spring applies a biasing force urging the pin outward from the driver head in a lateral direction perpendicular to the longitudinal direction such that in a deployed position a head portion of the pin extends laterally farther than an outside surface of the driver head and in a retracted position the spring is compressed within the recessed detent of the driver head, and wherein, in a stacked position, the first breakoff head of the first set screw is disposed on the magazine retention portion and the distal end of the surgical instrument is engaged with the second set screw.

8. The system of claim 7, wherein the surgical instrument further comprises a handle positioned on an end of the surgical instrument opposite the driver head.

9. The system of claim 7, wherein the first interlocking portion of the first breakoff head comprises a first groove, the second interlocking portion of the second breakoff head comprises a second groove, and wherein the at least one interlocking portion of the driver head comprises a protrusion.

10. The system of claim 7, wherein the first interlocking portion of the first breakoff head comprises a first protrusion, the second interlocking portion of the second breakoff head comprises a second protrusion, and wherein the at least one interlocking portion of the driver head comprises a groove.

11. The system of claim 7, wherein, in the stacked position, the at least one interlocking portion of the driver head is interlocked with the second interlocking portion of the second breakoff head, and the driver head is configured to break off the second breakoff head from the second threaded portion when rotated.

12. The system of claim 7, wherein:

the first set screw further comprises a first recessed area positioned on an inner surface of the first set screw and opposite to the first breakoff region, and the second set screw further comprises a second recessed area positioned on an inner surface of the second set screw and opposite to the second breakoff region.

13. The system of claim 12, wherein the first recessed area and the second recessed area are each formed in a shape complimentary to a semispherical shape of a distal end portion of the pin.

14. The system of claim 12, wherein a distal end portion of the pin is configured to be inserted into the second recessed area of the second set screw while the first breakoff portion is retained on the magazine retention portion.

15. The system of claim 14, wherein the distal end portion of the pin, positioned in the deployed state, is configured to prevent the first breakoff head, broken off the first set screw, from sliding off the driver head.

16. The system of claim 12, wherein a distal end portion of the pin, positioned in a deployed state, extends beyond an outer surface of the driver head, and wherein the distal end portion of the pin is configured to be inserted into the second recessed area of the second set screw while the first breakoff portion is retained on the magazine retention portion.

17. The system of claim 7, wherein, in an additional stacked position, the driver head is configured to retain the first breakoff head and the second breakoff head on the magazine portion in a position that is proximal relative to the pin.

18. The system of claim 7, wherein the driver head is configured to retain at least three broken off breakoff heads, including at least the first breakoff head and the second breakoff head.

* * * * *